United States Patent
Meiere

(10) Patent No.: US 7,332,618 B2
(45) Date of Patent: Feb. 19, 2008

(54) ORGANOMETALLIC PRECURSOR COMPOUNDS

(75) Inventor: Scott Houston Meiere, Williamsville, NY (US)

(73) Assignee: Praxair Technology, Inc., Danbury, CT (US)

(*) Notice: Subject to any disclaimer, the term of this patent is extended or adjusted under 35 U.S.C. 154(b) by 0 days.

(21) Appl. No.: 11/193,535

(22) Filed: Aug. 1, 2005

(65) Prior Publication Data

US 2006/0068102 A1 Mar. 30, 2006

(51) Int. Cl.
*C07F 5/00* (2006.01)
*C07F 5/06* (2006.01)
*C07F 7/00* (2006.01)
*C07F 7/02* (2006.01)
*C07F 7/28* (2006.01)
*C07F 7/30* (2006.01)
*C07F 9/00* (2006.01)
*C07F 11/00* (2006.01)

(52) U.S. Cl. .............................. 556/1; 556/42; 556/43; 556/51; 556/52; 556/53; 556/57; 556/58; 556/170; 556/176; 556/407

(58) Field of Classification Search ............ 427/126.3, 427/255.18, 255.19, 255.31, 255.34, 255.35, 427/255.36, 255.37; 106/287.11, 287.18, 106/287.19, 287.17, 287.2; 534/15; 546/2; 556/1, 42, 51, 57, 81, 176, 407, 43, 52, 53, 556/58, 170
See application file for complete search history.

(56) References Cited

U.S. PATENT DOCUMENTS

| | | | |
|---|---|---|---|
| 6,020,243 A | 2/2000 | Wallace et al. | 438/287 |
| 6,175,027 B1* | 1/2001 | Sullivan et al. | 556/53 |
| 6,291,867 B1 | 9/2001 | Wallace et al. | 257/410 |
| 2002/0175393 A1 | 11/2002 | Baum et al. | 257/506 |
| 2002/0187644 A1 | 12/2002 | Baum et al. | 438/700 |
| 2003/0111678 A1 | 6/2003 | Colombo et al. | 257/240 |

FOREIGN PATENT DOCUMENTS

| WO | WO0279211 A1 | 1/2002 |
|---|---|---|
| WO | WO 02/079211 | * 10/2002 |

OTHER PUBLICATIONS

Balboni et al, "Group 4 Dimethylmetallocenes: Improved Synthesis and Reactivity Studies", Inorg. Chem. 2001, 40, 6588-6597, (no month available).*
Bradley et al, "Metallo-organic Compounds containing Metal-Nitrogen bonds, Part I . . . ", J. Chem. Soc., pp. 3857-3861, Oct. 1960.*
Bradley et al, "Metallo-organic Compounds containing Metal-Nitrogen Bonds. Part III . . . ", Canadian Journal of Chemistry, pp. 1355-1360, Jul. 1962.*
G.E. Manoussakis et al., "Preparation Of Tetrakis (Pyrrolidino)-Silicon,-Germanium, -Tin and -Titanium", *Inorg. Nucl. Chem. Letters*, vol. 5, pp. 733-736, 1969, no month provided.

* cited by examiner

*Primary Examiner*—David M Brunsman
(74) *Attorney, Agent, or Firm*—Gerald L. Coon

(57) ABSTRACT

This invention relates to organometallic precursor compounds represented by the formula $(H)_mM(R)_n$ wherein M is a metal or metalloid, R is the same or different and is a substituted or unsubstituted, saturated or unsaturated, heterocyclic radical containing at least one nitrogen atom, m is from 0 to a value less than the oxidation state of M, n is from 1 to a value equal to the oxidation state of M, and m+n is a value equal to the oxidation state of M, a process for producing the organometallic precursor compounds, and a method for producing a film or coating from the organometallic precursor compounds.

12 Claims, No Drawings

ORGANOMETALLIC PRECURSOR COMPOUNDS

FIELD OF THE INVENTION

This invention relates to organometallic precursor compounds represented by the formula $(H)_mM(R)_n$ wherein M is a metal or metalloid, R is the same or different and is a substituted or unsubstituted, saturated or unsaturated, heterocyclic radical containing at least one nitrogen atom, m is from 0 to a value less than the oxidation state of M, n is from 1 to a value equal to the oxidation state of M, and m+n is a value equal to the oxidation state of M, a process for producing the organometallic precursor compounds, and a method for producing a film or coating from the organometallic precursor compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate. Preferably, chemical vapor deposition precursors are volatile, heat decomposable and capable of producing uniform films under chemical vapor deposition conditions.

The semiconductor industry is currently considering the use of thin films of various metals for a variety of applications. Many organometallic complexes have been evaluated as potential precursors for the formation of these thin films. A need exists in the industry for developing new compounds and for exploring their potential as chemical vapor deposition precursors for film depositions.

For the chemical vapor deposition of silicon-containing films (e.g., $SiO_2$), compounds such as silane, chlorinated silanes, and alkoxy silanes (e.g., TEOS) are well known. However, as next generation oxide materials with higher dielectric constants, so called 'high-k' materials (e.g., $HfO_2$), are integrated, and concurrently new precursors are developed for these materials (e.g., hafnium amides), other silicon precursors will require development for the deposition of ternary systems and beyond (e.g., hafnium silicates).

For silicon amide compounds with cyclic amide ligands, an example reported in the literature is tetrakis(pyrrolidinyl) silane (a solid at room temperature, mp=30° C.). Inorg. Nucl. Chem. Letters 1969 5 733 discloses tetrakis(pyrrolidinyl)silane compound and a low yield synthetic method for preparation thereof.

U.S. Patent Application Publication Nos. U.S. 2002/0187644 A1 and U.S. 2002/0175393 A1 disclose metalloamide precursor compositions having stated utility for forming dielectric thin films such as gate dielectric, high dielectric constant metal oxides, and ferroelectric metal oxides and to a low temperature chemical vapor deposition process for deposition of such dielectric thin films utilizing the compositions.

In developing methods for forming thin films by chemical vapor deposition or atomic layer deposition methods, a need continues to exist for precursors that preferably are liquid at room temperature, have adequate vapor pressure, have appropriate thermal stability (i.e., for chemical vapor deposition will decompose on the heated substrate but not during delivery, and for atomic layer deposition will not decompose thermally but will react when exposed to co-reactant), can form uniform films, and will leave behind very little, if any, undesired impurities (e.g., halides, carbon, etc.). Therefore, a need continues to exist for developing new compounds and for exploring their potential as chemical vapor or atomic layer deposition precursors for film depositions. It would therefore be desirable in the art to provide a precursor that possesses some, or preferably all, of the above characteristics.

SUMMARY OF THE INVENTION

This invention relates to organometallic precursor compounds represented by the formula $(H)_mM(R)_n$ wherein M is a metal or metalloid, R is the same or different and is a substituted or unsubstituted, saturated or unsaturated, heterocyclic radical containing at least one nitrogen atom, m is from 0 to a value less than the oxidation state of M, n is from 1 to a value equal to the oxidation state of M, and m+n is a value equal to the oxidation state of M, provided that R is other than unsubstituted pyrrolidinyl when M is Si and n is 4. More particularly, this invention relates to organometallic precursor compounds represented by the formula $(H)_mM(R)_n$ wherein M is a metal or metalloid, R is the same or different and is a substituted or unsubstituted, saturated or unsaturated, cyclic amido or amino radical, m is from 0 to a value less than the oxidation state of M, n is from 1 to a value equal to the oxidation state of M, and m+n is a value equal to the oxidation state of M, provided that R is other than unsubstituted pyrrolidinyl when M is Si and n is 4. Typically, M is selected from Si, Ti, Zr, Hf, V, Nb, Ta, Cr, Mo, W, Al, Ga, Ge, a Lanthanide series element or an Actinide series element, and R is selected from aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl.

This invention also relates to a process for the production of an organometallic compound comprising (i) reacting a heterocyclic compound containing at least one nitrogen atom with a base material in the presence of a solvent and under reaction conditions sufficient to produce a first reaction mixture comprising a heteroatom-containing compound, (ii) adding a metal source compound to said first reaction mixture, (iii) reacting said heteroatom-containing compound with said metal source compound under reaction conditions sufficient to produce a second reaction mixture comprising said organometallic compound, and (iv) separating said organometallic compound from said second reaction mixture. The organometallic compound yield resulting from the process of this invention can be 60% or greater, preferably 75% or greater, and more preferably 90% or greater.

This invention further relates to a method for producing a film, coating or powder by decomposing an organometallic precursor compound represented by the formula $(H)_mM(R)_n$ wherein M is a metal or metalloid, R is the same or different and is a substituted or unsubstituted, saturated or unsaturated, heterocyclic radical containing at least one nitrogen atom, m is from 0 to a value less than the oxidation state of M, n is from 1 to a value equal to the oxidation state of M, and m+n is a value equal to the oxidation state of M, provided that R is other than unsubstituted pyrrolidinyl when M is Si and n is 4, thereby producing the film, coating or powder. Typically, the decomposing of said organometallic precursor compound is thermal, chemical, photochemical or plasma-activated.

This invention also relates to organometallic precursor mixtures comprising (i) a first organometallic precursor compound represented by the formula $(H)_m M(R)_n$ wherein M is a metal or metalloid, R is the same or different and is a substituted or unsubstituted, saturated or unsaturated, heterocyclic radical containing at least one nitrogen atom, m is from 0 to a value less than the oxidation state of M, n is from 1 to a value equal to the oxidation state of M, and m+n is a value equal to the oxidation state of M, provided that R is other than unsubstituted pyrrolidinyl when M is Si and n is 4, and (ii) one or more different organometallic precursor compounds (e.g., a hafnium-containing, tantalum-containing or molybdenum-containing organometallic precursor compound).

This invention relates in particular to 'next generation' depositions involving amide-based silicon precursors. These precursors have been shown to have advantages over the other known precursors, especially when utilized in tandem with other 'next-generation' materials (e.g., hafnium, tantalum and molybdenum), for the formation of silicates, silicon oxynitrides, and the like. These silicon-containing materials can be used for a variety of purposes such as dielectrics, barriers, and electrodes, and in many cases show improved properties (thermal stability, desired morphology, less diffusion, lower leakage, less charge trapping, and the like) than the non-silicon containing films.

The invention has several advantages. For example, the method of the invention is useful in generating organometallic compound precursors that have varied chemical structures and physical properties. Films generated from the organometallic compound precursors can be deposited with a short incubation time, and the films deposited from the organometallic compound precursors exhibit good smoothness.

This invention relates in particular to chemical vapor deposition and atomic layer deposition precursors for next generation devices, specifically heterocyclic-containing precursors that are liquid at room temperature, i.e., 20° C.

DETAILED DESCRIPTION OF THE INVENTION

As indicated above, this invention relates to organometallic precursor compounds represented by the formula $(H)_m M(R)_n$ wherein M is a metal or metalloid, R is the same or different and is a substituted or unsubstituted, saturated or unsaturated, heterocyclic radical containing at least one nitrogen atom, m is from 0 to a value less than the oxidation state of M, preferably from 0 to 3, n is from 1 to a value equal to the oxidation state of M, preferably from 1 to 4, and m+n is a value equal to the oxidation state of M, provided that R is other than unsubstituted pyrrolidinyl when M is Si and n is 4. Typically, R is the same or different and is a substituted or unsubstituted, saturated or unsaturated, cyclic amido or amino radical and is selected from aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl. Typically, M is selected from Si, Ti, Zr, Hf, V, Nb, Ta, Cr, Mo, W, Al, Ga, Ge, a Lanthanide series element or an Actinide series element.

In a preferred embodiment, this invention relates to organometallic precursor compounds represented by the formula $M(R)_{n'}$ wherein M is a metal or metalloid, R is the same or different and is a substituted or unsubstituted, saturated or unsaturated, heterocyclic radical containing at least one nitrogen atom, and n' is a value equal to the oxidation state of M, provided that R is other than unsubstituted pyrrolidinyl when M is Si and n' is 4.

Illustrative organometallic precursor compounds of this invention include, for example, tetrakis(pyrrolyl)silane, tetrakis(2-methylpyrrolidinyl)silane, tetrakis(imidazolyl)silane, bis(pyrrolidinyl)(pyrrolyl)(piperidinyl)silane, tetrakis(1-methylpiperazinyl)silane, tetrakis(pyrazolyl)silane, tris(pyrrolyl)silane, bis(pyrrolyl)silane, pyrrolylsilane, tris(2-methylpyrrolidinyl)silane, bis(2-methylpyrrolidinyl)silane, 2-methylpyrrolidinylsilane, tris(imidazolyl)silane, bis(imidazolyl)silane, imidazolylsilane, tris(1-methylpiperazinyl)silane, bis(1-methylpiperazinyl)silane, 1-methylpiperazinylsilane, tris(pyrazolyl)silane, bis(pyrazolyl)silane, pyrazolylsilane, and the like.

The organometallic precursor compounds of this invention may be homoleptic, i.e., all R radicals are the same such as tetrakis(2-methylpyrrolidinyl)silane, or heteroleptic, i.e., one or more of the R radicals are different from each other such as bis(pyrrolidinyl)(pyrrolyl)(piperidinyl)silane.

The cyclic amide silane compounds of this invention comprise one of more of the following: (1) unsaturated, conjugated and/or aromatic heterocyclic systems, (2) functionalized heterocyclic ring substituents, and (3) multiple heteroatoms within the heterocyclic ring.

A pyrrole ($HNC_4H_4$) complex is an example of an aromatic heterocyclic system. A five membered aromatic heterocycle, the differences between pyrrole and pyrrolidine have been well documented. The basicity for pyrrole itself is significantly lower than its saturated analog pyrrolidine (pKa=0, ~11 respectively) due to the 'tying up' of the 'pi' nitrogen lone pair in aromaticity. However, many complexes of pyrrolides with transition metals have been reported (eta-1 as well as eta-5). For the eta-1 binding mode, the deprotonated pyrrole utilizes one available lone pair for sigma-type binding. However, the remaining lone pair is not as available for ligand-to-metal pi donation due to aromaticity commitments. Therefore, a pyrrolyl complex of silicon (e.g., tris, tetrakis) may be stable under inert conditions at room temperature, but may be more reactive and/or decompose more quickly under deposition conditions. This property could be beneficial to controlling silicon incorporation. The mono unsaturated systems (and therefore non-aromatic) pyrrolines ($HNC_4H_6$) with silicon may be rather reactive.

Another method of weakening the silicon nitrogen bond of pyrrolidinyl silicon complexes would be to impose destabilizing steric effects around the bond itself (e.g., substituents at the adjacent carbons). The compound 2-methylpyrrolidine would likely weaken the Si—N bond. The asymmetry created by the additional methyl group would likely lower the melting point as compared to the parent system, thus yielding a more desirable liquid precursor. Other materials with additional bulk at the 2 position are 2-pyrrolidinone and succinimide, both of which are 'amides' in the sense that the nitrogen is conjugated to a carbonyl group. This situation would lead to a scenario similar to the pyrrole case: poor availability of one of the lone pairs due to resonance effects.

There are also heterocycles with more than one heteroatom, such as the aromatics imidazole (two nitrogens) and triazole (three nitrogens) or the non-aromatic thiazolidine. These compounds may produce interesting deposition properties due to the interaction between the non-bonded heteroatom with the substrates/films. They may also effect the stability of the Si—N bond, volatility, and melting point.

As also indicated above, this invention also relates to a process for the production of an organometallic compound comprising (i) reacting a heterocyclic compound containing at least one nitrogen atom with a base material in the presence of a solvent and under reaction conditions sufficient to produce a first reaction mixture comprising a heteroatom-containing compound, (ii) adding a metal source compound to said first reaction mixture, (iii) reacting said heteroatom-containing compound with said metal source compound under reaction conditions sufficient to produce a second reaction mixture comprising said organometallic compound, and (iv) separating said organometallic compound from said second reaction mixture. The organometallic compound yield resulting from the process of this invention can be 60% or greater, preferably 75% or greater, and more preferably 90% or greater. The process is particularly well-suited for large scale production since it can be conducted using the same equipment, some of the same reagents and process parameters that can easily be adapted to manufacture a wide range of products. The process provides for the synthesis of organometallic compounds using a process where all manipulations can be carried out in a single vessel, and which route to the organometallic compounds does not require the isolation of an intermediate complex. This process is more fully described in U.S. patent application Ser. No. 10/678,074, filed Oct. 6, 2003, which is incorporated herein by reference.

The organometallic precursor compounds of this invention may also be prepared by conventional processes such as described in Legzdins, P. et al. Inorg. Synth. 1990, 28, 196 and references therein.

The metal source compound, e.g., $SiCl_4$, trichlorosilane and the like, starting material may be selected from a wide variety of compounds known in the art. The invention herein most prefers metals selected from Si, Ti, Zr, Hf, V, Nb, Ta, Cr, Mo, W, Al, Ga, Ge, a Lanthanide series element or an Actinide series element.

The concentration of the metal source compound starting material can vary over a wide range, and need only be that minimum amount necessary to react with the heterocyclic compound containing at least one nitrogen atom and to provide the given metal concentration desired to be employed and which will furnish the basis for at least the amount of metal necessary for the organometallic compounds of this invention. In general, depending on the size of the reaction mixture, metal source compound starting material concentrations in the range of from about 1 millimole or less to about 10,000 millimoles or greater, should be sufficient for most processes.

The heterocyclic compounds containing at least one nitrogen atom may be selected from a wide variety of compounds known in the art. Illustrative heterocyclic compounds containing at least one nitrogen atom include, for example, cyclic amines, cyclic amides and the like. Preferred heterocyclic compound starting materials include aziridines, azetidines, pyrrolidines, thiazolidines, piperidinyes, pyrroles, pyridines, pyrimidines, pyrrolines, pyrazoles, thiazoles, oxazoles, imidazoles, imidazolidinones, imidazolidinethiones, quinolines, isoquinolines, carbazoles, triazoles, indoles, purines and the like.

The concentration of the heterocyclic compound starting material containing at least one nitrogen atom can vary over a wide range, and need only be that minimum amount necessary to react with the base starting material. In general, depending on the size of the reaction mixture, heterocyclic compound starting material concentrations in the range of from about 1 millimole or less to about 10,000 millimoles or greater, should be sufficient for most processes.

The base starting material may be selected from a wide variety of compounds known in the art. Illustrative bases include any base with a pKa greater than about 10, preferably greater than about 20, and more preferably greater than about 25. The base material is preferably n-BuLi, t-BuLi, MeLi, NaH, CaH, lithium amides and the like.

The concentration of the base starting material can vary over a wide range, and need only be that minimum amount necessary to react with the heterocyclic compound starting material. In general, depending on the size of the first reaction mixture, base starting material concentrations in the range of from about 1 millimole or less to about 10,000 millimoles or greater, should be sufficient for most processes.

In one embodiment, the heteroatom-containing compound may be generated in situ, for example, lithiated cyclic amides, lithiated cyclic amines and the like. Generating the heteroatom-containing compound in situ in the reaction vessel immediately prior to reaction with the metal source compound is beneficial from a purity standpoint by eliminating the need to isolate and handle any reactive solids. It is also less expensive.

With the in situ generated heteroatom-containing compound in place, addition of the metal source compound, e.g., $SiCl_4$, can be performed through solid addition, or in some cases more conveniently as a solvent solution or slurry. Although certain metal source compounds are moisture sensitive and are used under an inert atmosphere such as nitrogen, it is generally to a much lower degree than the heteroatom-containing compounds, for example, lithiated amides, amines and the like. Furthermore, many metal source compounds are denser and easier to transfer.

The heteroatom-containing compounds prepared from the reaction of the heterocyclic compound starting material containing at least one nitrogen atom and the base starting material may be selected from a wide variety of compounds. Illustrative heteroatom-containing compounds include, for example, lithiated cyclic amides, lithiated cyclic amines and the like.

The concentration of the heteroatom-containing compounds can vary over a wide range, and need only be that minimum amount necessary to react with the metal source compounds to give the organometallic compounds of this invention. In general, depending on the size of the reaction mixture, heteroatom-containing compound concentrations in the range of from about 1 millimole or less to about 10,000 millimoles or greater, should be sufficient for most processes.

The solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitrites, silicone oils, other aprotic solvents, or mixtures of one or more of the above; more preferably, diethylether, pentanes, or dimethoxyethanes; and most preferably hexanes or THF. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the base starting material with the heterocyclic compound containing at least one nitrogen atom, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

Reaction conditions for the reaction of the heteroatom-containing compound with the metal source compound, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps. In the embodiment of this invention which is carried out in a single pot, the heteroatom-containing compound is not separated from the first reaction mixture prior to reacting with the metal source compound. In a preferred embodiment, the metall source compound is added to the first reaction mixture at ambient temperature or at a temperature greater than ambient temperature.

The organometallic compounds prepared from the reaction of the heteroatom-containing compound and the metal source compound may be selected from a wide variety of compounds. For purposes of this invention, organometallic compounds include compounds having a metal-heteroatom bond. Illustrative organometallic compounds include, for example, cyclic amides, cyclic amines and the like.

For organometallic compounds prepared by the method of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

The organometallic compound precursors described herein are preferably liquid at room temperature, i.e., 20° C., and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention relates to organometallic precursor mixtures comprising (i) a first organometallic precursor compound represented by the formula $(H)_m M(R)_n$ wherein M is a metal or metalloid, R is the same or different and is a substituted or unsubstituted, saturated or unsaturated, heterocyclic radical containing at least one nitrogen atom, m is from 0 to a value less than the oxidation state of M, n is from 1 to a value equal to the oxidation state of M, and m+n is a value equal to the oxidation state of M, provided that R is other than unsubstituted pyrrolidinyl when M is Si and n is 4, and (ii) one or more different organometallic precursor compounds (e.g., a hafnium-containing, tantalum-containing or molybdenum-containing organometallic precursor compound).

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors, ammonia and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

As indicated above, this invention also relates in part to a method for producing a film, coating or powder. The method includes the step of decomposing at least one organometallic compound precursor, thereby producing the film, coating or powder, as further described below.

Deposition methods described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, Ta; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometers thick. Films that are less than 50 nanometer thick, for instance, films that have a thickness between about 1 and about 20 nanometers, also can be produced.

Organometallic compound precursors described above also can be employed in the method of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above, an organometallic compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

A dry three liter, three-neck round bottom flask was charged with a magnetic stirbar and fitted with two septum (outer necks) and a 500 milliliter equalizing graduated addition funnel (center neck, capped with a septum). One side neck septum was fitted with a thermocouple lead. To the flask via cannula, "BuLi (1 liter 2.5 M hexane solution, 2.5 mol) was added along with additional anhydrous hexanes (530 milliliters). To the addition funnel was added hexanes (125 milliliters), then pyrrolidine (240 milliliters, 204.5 grams, 2.88 mol). The flask was placed into an ice water bath and cooled to about 0° C. With stirring, the contents of the addition funnel were slowly added dropwise to the reaction flask at such a rate as to keep the reaction temperature less than 5° C. (about 5 hours). The reaction was allowed to warm slowly to about 22° C. and stirring was continued overnight (about 14 hours) under a slow nitrogen purge. To the resulting thick cream-colored suspension was added THF (500 milliliters), which dissolved the solids. The resulting solution was cooled to about 0° C. in an ice water bath. To the addition funnel was added THF (70 milliliters) and $SiCl_4$ (70 milliliters, 103.8 grams, 0.61 mol). The contents of the addition funnel were slowly added dropwise to the reaction flask at such a rate as to keep the reaction temperature less than 10° C. (about 4 hours). The reaction was allowed to warm slowly to about 22° C. and stirring was continued overnight (about 14 hours) under a slow nitrogen purge. The solvents were removed by atmospheric distillation (max head temperature about 65° C.). The product was then collected by vacuum distillation (head temperature about 125° C. at about 0.2 torr) into a tared receiver flask within an ice water bath (about 0° C.). Yield of the colorless white solid was 179.9 grams (0.58 mol, 96%). The product was analyzed to be greater than 99% pure. $^1$H NMR (400 MHz, toluene-$d_8$, δ): 3.07 (m, α-H), 1.65 (m, β-H). GC-MS: Parent ion 308 m/e observed (GC-FID also run). DSC: mp=30-31° C. TGA: <1% residue.

The above method produced tetrakis(pyrrolidinyl)silane. The preparation reported by Manoussakis and Tossidis in 1969 yielded the compound at 50%, whereas the above synthesis resulted in 96% yield (and did not require any external heating). Similar methods as above should find utility for the synthesis of analogous compounds (e.g., tetrakis(pyrrolyl)silane, tetrakis(2-methylpyrrolidinyl)silane, tetrakis(imidazolyl)silane, and the like).

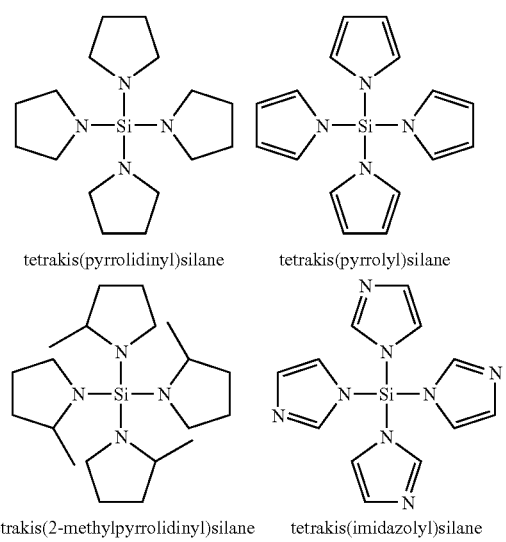

tetrakis(pyrrolidinyl)silane   tetrakis(pyrrolyl)silane tetrakis(2-methylpyrrolidinyl)silane   tetrakis(imidazolyl)silane

The invention claimed is:
1. A process for the production of an organometallic compound comprising (i) reacting a heterocyclic compound containing at least one nitrogen atom with a base material in the presence of a solvent and under reaction conditions sufficient to produce a first reaction mixture comprising a heteroatom-containing compound, (ii) adding a metal source compound to said first reaction mixture, (iii) reacting said heteroatom-containing compound with said metal source compound under reaction conditions sufficient to produce a second reaction mixture comprising said organometallic compound, and (iv) separating said organometallic compound from said second reaction mixture.

2. The process of claim 1 wherein the organometallic compound is a liquid at 20° C.

3. The process of claim 1 wherein the organometallic compound yield is 60% or greater.

4. The process of claim 1 wherein the base material has a pKa greater than about 10.

5. The process of claim 1 wherein the heteroatom-containing compound comprises a lithiated cyclic amine or amide.

6. The process of claim 1 wherein the metal source compound is represented by the formula $(H)_m M(X)_n$ wherein M is Si, Ti, Zr, Hf, V, Nb, Ta, Cr, Mo, W, Al, Ga, Ge, a Lanthanide series element or an Actinide series element, X is halide, m is from 0 to a value less than the oxidation state of M, n is from 1 to a value equal to the oxidation state of M, and m+n is a value equal to the oxidation state of M.

7. The process of claim 1 wherein the organometallic compound is represented by the formulas $(H)_m M(R)_n$ wherein M is a metal or metalloid, R is the same or different and is selected from (i) a substituted, saturated heterocyclic radical containing at least one nitrogen atom and (ii) a substituted or unsubstituted, unsaturated heterocyclic radical containing at least one nitrogen atom, m is from 0 to a value less than the oxidation state of M, n is from 1 to a value equal to the oxidation state of M, and m+n is a value equal to the oxidation state of M, provided that R is other than unsubstituted pyrrolidinyl when M is Si and n is 4.

8. The process of claim 7 wherein R is a cyclic amino or amido radical.

9. The process of claim 7 wherein M is Si, Ti, Zr, Hf, V, Nb, Ta, Cr, Mo, W, Al, Ga, Ge, a Lanthanide series element or an Actinide series element.

10. The process of claim 7 wherein R is the same or different and is a substituted, saturated heterocyclic radical containing at least one nitrogen atom selected from aziridinyl, azetidinyl, pyrrolidinyl, thiazolidinyl and piperidinyl.

11. The process of claim 7 wherein R is the same or different and is a substituted or unsubstituted, unsaturated heterocyclic radical containing at least one nitrogen atom selected from pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl.

12. The process of claim 1 wherein the organometallic compound is selected from tetrakis(pyrrolyl)silane, tetrakis(2-methylpyrrolidinyl)silane, tetrakis(imidazolyl)silane, bis(pyrrolidinyl)(pyrrolyl)(piperidinyl)silane, tetrakis(1-methylpyrrolidinyl)silane, tetrakis(pyrazolyl)silane, tris(pyrrolyl)silane, bis(pyrrolyl)silane, pyrrolylsilane, tris(2-methylpyrrolidinyl)silane, bis(2-methylpyrrolidinyl)silane, 2-methylpyrroildinylsilane, tris(imidazolyl)silane, bis(imidazolyl)silane, imidazolylsilane, tris(1-methylpiperazinyl)silane, bis(1-methylpiperazinyl)silane, 1-methylpiperazinylsilane, tris(pyrazolyl)silane, bis(pyrazolyl)silane, and pyrazolylsilane.

* * * * *